(12) United States Patent
Smith

(10) Patent No.: US 10,131,928 B2
(45) Date of Patent: Nov. 20, 2018

(54) INOSITOL BIOTRANSFORMATION

(71) Applicant: University Court of the University of St Andrews, St Andrews, Fife (GB)

(72) Inventor: Terry K. Smith, Fife (GB)

(73) Assignee: UNIVERSITY COURT OF THE UIVERSITY OF ST ANDREWS, St Andrews, Fife (GB)

(*) Notice: Subject to any disclaimer, the term of this patent is extended or adjusted under 35 U.S.C. 154(b) by 74 days.

(21) Appl. No.: 14/902,804

(22) PCT Filed: Jun. 24, 2014

(86) PCT No.: PCT/GB2014/051920
§ 371 (c)(1),
(2) Date: Jan. 4, 2016

(87) PCT Pub. No.: WO2015/001312
PCT Pub. Date: Jan. 8, 2015

(65) Prior Publication Data
US 2016/0168607 A1    Jun. 16, 2016

(30) Foreign Application Priority Data

Jul. 4, 2013  (GB) .................................. 1311989.6

(51) Int. Cl.
| C12P 7/02 | (2006.01) |
|---|---|
| C12P 7/24 | (2006.01) |
| C12Q 1/42 | (2006.01) |
| C12Q 1/48 | (2006.01) |
| C12P 19/02 | (2006.01) |
| G01N 33/68 | (2006.01) |

(52) U.S. Cl.
CPC .................................. *C12P 19/02* (2013.01)

(58) Field of Classification Search
CPC ... C12P 19/02; C12P 7/02; C12Q 1/48; C12Q 1/42; C12Q 1/485; G01N 2333/395; G01N 2500/10; G01N 33/6818; G01N 33/6845; G01N 33/6848
USPC .................................. 435/105, 156; 568/763
IPC .................. C12P 7/02,7/24; C12Q 1/42, 1/48, C12Q 1/485; G01N 33/68
See application file for complete search history.

(56) References Cited

U.S. PATENT DOCUMENTS 8,178,704 B2 * 5/2012 Bazin ....................... C07F 9/117
435/7.1

FOREIGN PATENT DOCUMENTS

| WO | WO 2003/004141 A2 | 1/2003 |
| WO | WO 2006/059052 A2 | 6/2006 |
| WO | WO 2015/001312 A1 | 1/2015 |

OTHER PUBLICATIONS

Smart et al. 1993. A plant gene with homology to o-myo-inositol-3-phosphate synthase is rapidly and spatially up-regulated during an abscisic-acid-induced morphogenic response in Spirodela polyrhiza. The Plant Journal, vol. 4, No. 2, pp. 279-293.*
Loewus et al. 1980. Stereochemistry of the myo-Inositol-1-phosphate Synthase Reaction. Journal of Biological Chemistry, vol. 255, No. 34, pp. 11719-11712.*
Eisenberg et al.1987. Measurement of Biosynthesis of myo-Inositol from Glucose 6-Phosphate. Methods in Enzymology, vol. 141, pp. 127-141.*
Hallcher et al. 1980. The Effects of Lithium Ion and Other Agents on the Activity of myo-Inositol-1-phosphatase from Bovine Brain. Journal of Biological Chemistry, vol. 255, No. 22, pp. 10896-10901.*
Parker et al 2010. High fructose corn syrup: Production, uses and public health concerns. Biotechnology and Molecular Biology Review, vol. 5, No. 5, pp. 71-78.*
Donahue et al. 1981. myo-Inositol-1-phosphate Synthase. Characteristics of the Enzyme and Identification of its Structural Gene in Yeast. The Journal of Biological Chemistry, vol. 256, No. 13, pp. 7077-7085.*
Bornhorst et al. 2000. Methods in Enzymology. Volume 326, pp. 245-254. (Year: 2000).*
International Search Report and Written Opinion from International Application No. PCT/GB2014/051920 dated Oct. 17, 2014, application now published as International Publication No. WO2015/001312 on Jan. 8, 2015.
Martin and Smith, "The glycosylphosphatidylinositol (GPI) biosynthetic pathway of bloodstream-form Trypanosoma brucei is dependent on the de novo synthesis of inositol", Molecular Microbiology, vol. 61, No. 1, pp. 89-105 (2006).
Mercier et al., "Synthesis of optically active derivatives of myo-inositol : Preparation of 1 I-myo-inositol 1-phosphate", Tetrahedron, vol. 25, Issue 23, pp. 5681-5687 (1969).
Pittner, "Influence of urea and organic solvents on the activity of immobilizedmyo-inositol-1-phosphate synthase containing active, self-regenerating coenzyme (NAD(+)) on the same matrix", Applied Biochemistry and Biotechnology, vol. 6, No. 2, pp. 153-166 (1981).
Potter and Lampe, "Chemistry of Inositol Lipid Mediated Cellular Signaling", Angew. Chemie Int. Ed. Engl., vol. 34, Issue 18, pp. 1933-1972 (1995).

(Continued)

*Primary Examiner* — Louise Humphrey
*Assistant Examiner* — Kailash C Srivastava
(74) *Attorney, Agent, or Firm* — McDermott Will & Emery LLP

(57) ABSTRACT

Disclosed is a method of preparing pure or substantially pure D-myo-inositol-3-phosphate from glucose-6-phosphate and/or fructose-6-phosphate. The method may also be applied to protected and/or derivative forms of glucose-6-phosphate and/or fructose-6-phosphate so as to form protected/derivative forms of D-myo-inositol-3-phosphate, for use in further chemical reactions. The enzyme D-myo-inositol-3-phosphate synthase (INO1) is contacted with the glucose-6-phosphate and/or fructose-6-phosphate to generate labeled or unlabeled, protected or unprotected D-myo-inositol-3-phosphate, which may be further reacted and/or purified.

17 Claims, 5 Drawing Sheets

Figure 1:
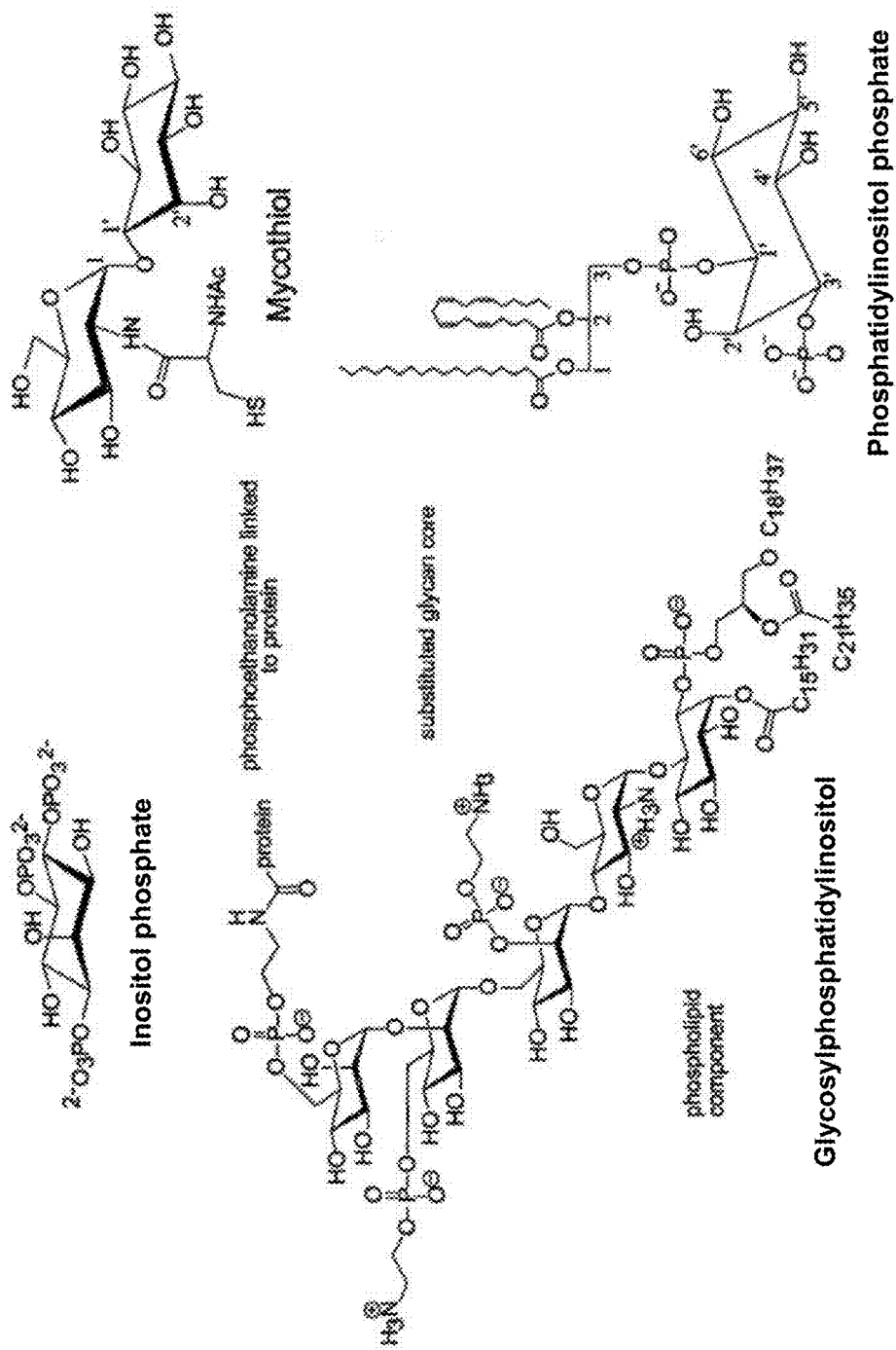

Specification includes a Sequence Listing.

(56) References Cited

OTHER PUBLICATIONS

Raychaudhuri et al, "L-myo-Inositol 1-Phosphate Synthase from Plant Sources (Characteristics of the Chloroplastic and Cytosolic Enzymes)", Plant Physiol., vol. 115, No. 2, pp. 727-736.

Spiers et al., "Structure of (+/−)-1,2;4,5-di-O-cyclohexylidene myo-inositol and synthesis of myo-inositol 3-phosphate via its phosphorylation with (2R,4S,5R)-2-chloro-3,4-dimethyl-5-phenyl-1,3,2-oxazaphospholidin-2-one", Carbohydrate Research, vol. 302, pp. 43-51 (1997).

\* cited by examiner

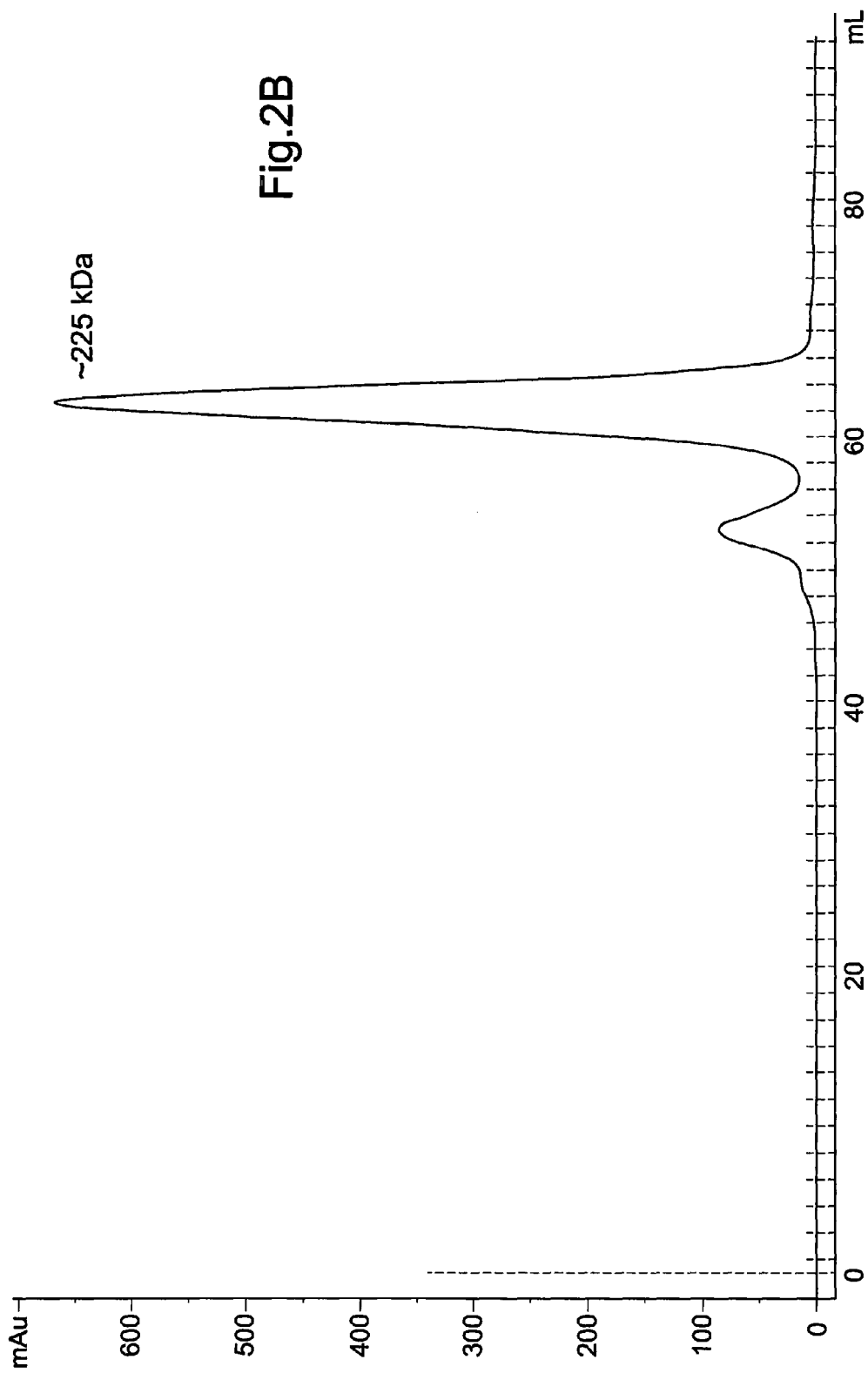

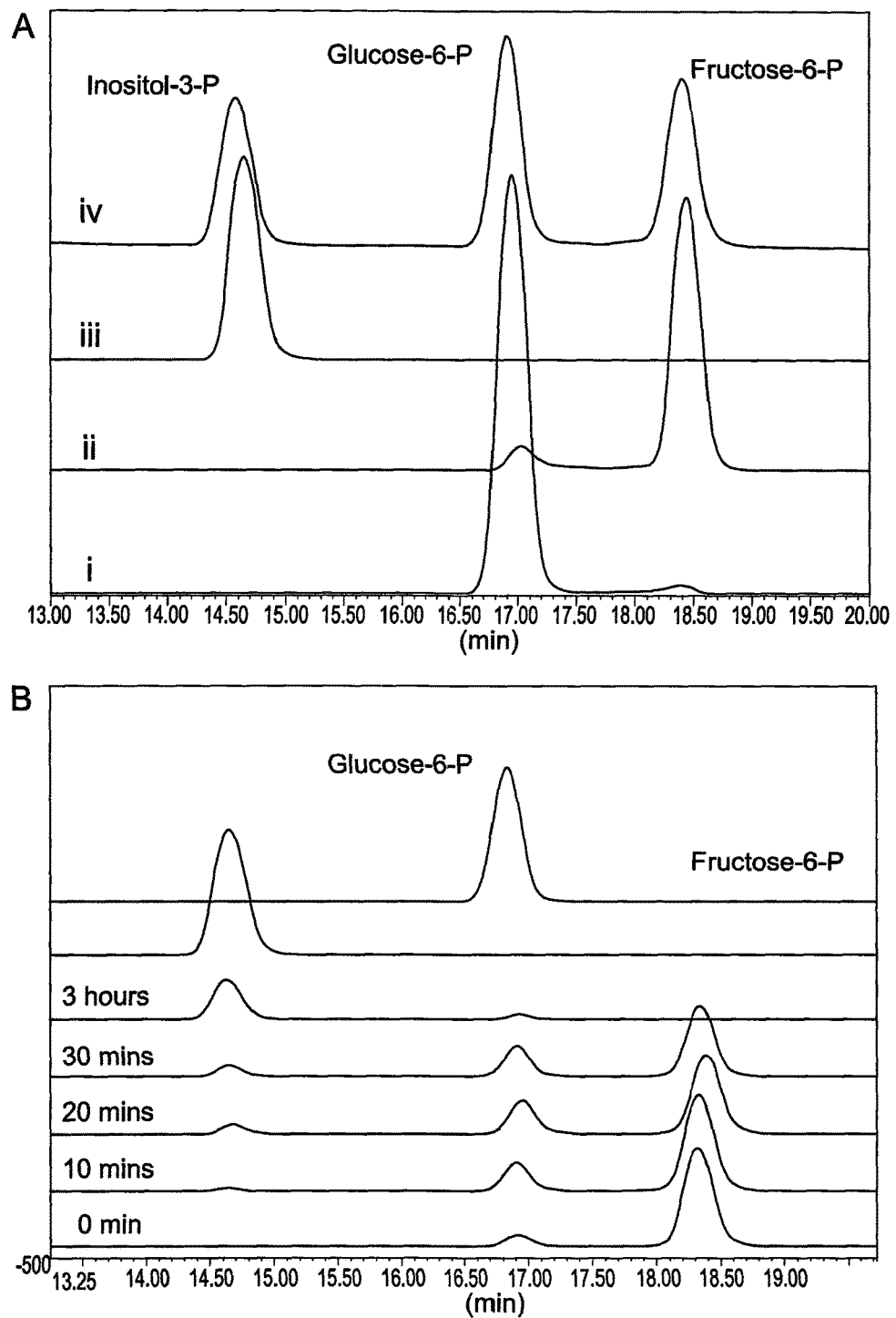

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Primers for amplifying DNA

<400> SEQUENCE: 1
ctcgagatgc cagccgtccg tacg            24

<210> SEQ ID NO 2
<211> LENGTH: 24
<212> TYPE: DNA
<213> ORGANISM: Artificial Sequence
<220> FEATURE:
<223> OTHER INFORMATION: Primers for amplifying DNA

<400> SEQUENCE: 2
ggatcctcaa cttcccacgc cgcc            24

<210> SEQ ID NO 3
<211> LENGTH: 37
<212> TYPE: DNA
<213> ORGANISM: Artificial Sequence
<220> FEATURE:
<223> OTHER INFORMATION: Primers for amplifying DNA

<400> SEQUENCE: 3
gttgttgggg atgactttgc aagtggtcaa acaaagg         37

<210> SEQ ID NO 4
<211> LENGTH: 37
<212> TYPE: DNA
<213> ORGANISM: Artificial Sequence
<220> FEATURE:
<223> OTHER INFORMATION: Primers for amplifying DNA

<400> SEQUENCE: 4
cctttgtttg accacttgca aagtcatccc caacaac         37

<210> SEQ ID NO 5

```
<211> LENGTH: 34
<212> TYPE: DNA
<213> ORGANISM: Artificial Sequence
<220> FEATURE:
<223> OTHER INFORMATION: Primers for amplifying DNA

<400> SEQUENCE: 5
atcttggcaa taatgccgga tataacttgg cagc                               34

<210> SEQ ID NO 6
<211> LENGTH: 34
<212> TYPE: DNA
<213> ORGANISM: Artificial Sequence
<220> FEATURE:
<223> OTHER INFORMATION: Primers for amplifying DNA

<400> SEQUENCE: 6
gctgccaagt tatatccggc attattgcca agat                               34

<210> SEQ ID NO 7
<211> LENGTH: 43
<212> TYPE: DNA
<213> ORGANISM: Artificial Sequence
<220> FEATURE:
<223> OTHER INFORMATION: Primers for amplifying DNA

<400> SEQUENCE: 7
ccccaaagca gtttcgttcg gcggaggtta cgaaaggcgg tgt                     43

<210> SEQ ID NO 8
<211> LENGTH: 43
<212> TYPE: DNA
<213> ORGANISM: Artificial Sequence
<220> FEATURE:
<223> OTHER INFORMATION: Primers for amplifying DNA

<400> SEQUENCE: 8
acaccgcctt tcgtaacctc cgccgaacga aactgctttg ggg                     43

<210> SEQ ID NO 9
<211> LENGTH: 43
<212> TYPE: DNA
<213> ORGANISM: Artificial Sequence
<220> FEATURE:
<223> OTHER INFORMATION: Primers for amplifying DNA

<400> SEQUENCE: 9
cgttcgaagg aggttacggc aggcggtgtg ctggacgata tgg                     43

<210> SEQ ID NO 10
<211> LENGTH: 43
<212> TYPE: DNA
<213> ORGANISM: Artificial Sequence
<220> FEATURE:
<223> OTHER INFORMATION: Primers for amplifying DNA

<400> SEQUENCE: 10
ccatatcgtc cagcacaccg cctgccgtaa cctccttcga acg                     43

<210> SEQ ID NO 11
<211> LENGTH: 43
<212> TYPE: DNA
<213> ORGANISM: Artificial Sequence
<220> FEATURE:
<223> OTHER INFORMATION: Primers for amplifying DNA

<400> SEQUENCE: 11
```

-continued

```
ctcccgtatg tgggtgacag cgcacgtgca ttggatgagt aca                43

<210> SEQ ID NO 12
<211> LENGTH: 43
<212> TYPE: DNA
<213> ORGANISM: Artificial Sequence
<220> FEATURE:
<223> OTHER INFORMATION: Primers for amplifying DNA

<400> SEQUENCE: 12
tgtactcatc caatgcacgt gcgctgtcac ccacatacgg gag                43

<210> SEQ ID NO 13
<211> LENGTH: 45
<212> TYPE: DNA
<213> ORGANISM: Artificial Sequence
<220> FEATURE:
<223> OTHER INFORMATION: Primers for amplifying DNA

<400> SEQUENCE: 13
ggtgctccat aaacacatgcc aggcctcgtt gctggctgca ccact             45

<210> SEQ ID NO 14
<211> LENGTH: 45
<212> TYPE: DNA
<213> ORGANISM: Artificial Sequence
<220> FEATURE:
<223> OTHER INFORMATION: Primers for amplifying DNA

<400> SEQUENCE: 14
agtggtgcag ccagcaacga ggcctggcat gtgttatgga gcacc              45

<210> SEQ ID NO 15
<211> LENGTH: 40
<212> TYPE: DNA
<213> ORGANISM: Artificial Sequence
<220> FEATURE:
<223> OTHER INFORMATION: Primers for amplifying DNA

<400> SEQUENCE: 15
acttttatct tacttgctgg cggctccacg tgtgccggag                    40

<210> SEQ ID NO 16
<211> LENGTH: 40
<212> TYPE: DNA
<213> ORGANISM: Artificial Sequence
<220> FEATURE:
<223> OTHER INFORMATION: Primers for amplifying DNA

<400> SEQUENCE: 16
ctccggcaca cgtggagccg ccagcaagta agataaaagt                    40
```

INOSITOL BIOTRANSFORMATION

CROSS-REFERENCE TO RELATED APPLICATIONS

This application is a U.S. National Stage of International Patent Application No. PCT/GB2014/051920, filed Jun. 24, 2014, which claims the benefit of priority to GB Patent Application No. 1311989.6 filed Jul. 4, 2013, each of which is hereby incorporated by reference in its entirety.

REFERENCE TO A SEQUENCE LISTING

A Sequence Listing is submitted with this application in the form of a text file, created Jan. 4, 2016, and titled "07716501268017seqlist.txt" (3,524 bytes), the contents of which are incorporated herein by reference in their entirety.

FIELD OF THE INVENTION

The present invention relates to the biotransformation (i.e. employing an enzyme) of glucose-6-phosphate or fructose-6-phosphate to D-myo-inositol-3-phosphate and derivatives and/or protected versions thereof. The D-myo-inositol-3-phosphate can be optionally protected and employed in further chemical synthesis to yield a variety of chemical moieties.

INTRODUCTION

The metabolism of myo-inositol plays a vital role in growth regulation, signal transduction, membrane, biogenesis, osmotolerance and other essential biochemical processes. In prokaryotes inositol is found sparingly, an example of an exception is mycobacteria, where it is essential for biogenesis of mycothiol, phosphatidyl inositol (PI), and glycosylphosphatidylinositol (GPIs) (see FIG. 1).

The synthesis of modified phosphorlyated inositol derivatives has a number of obstacles and challenges. The synthesis of a stereospecific protected myo-inositol can require multiple, such as 8-12 steps involving various protection, deprotection, resolution steps, such as 10-12, steps. Although myo-inositol is considered a carbohydrate it is not a usual carbohydrate as it has no anomeric carbon. However, much of the chemistry and difficulties involved in selectively protecting inositols is the same as in classical carbohydrate chemistry. A lot of hard work has gone into discovering how to protect specific hydroxyls in myo-inositol and leave others unprotected [Potter et al 1995, Cottaz et al 1995] in order to successfully phosphorlyate certain positions. Also, some research has been done using different starting materials such as D-pinitol and L-quebrachitol [Tegge and Ballou 1989]. Nevertheless all such synthetic routes are problematic and demanding.

There is thus a desire to be able to reduce the multiple steps required to form stereo-selectively protected myo-inositol that are used in the synthesis of numerous important biological compounds and reagents used for biomedical research.

The de novo synthesis of myo-inositol is a ubiquitous process occurring in almost all eukaryotes studied. It is the result of the concerted actions of two enzymes; firstly an D-myo-inositol-3-phosphate synthase (INO1) which isomerises glucose-6-phosphate to D-myo-inositol-3-phosphate; secondly, an inositol monophosphatase (IMPase) which dephosphorylates the D-myo-inositol-3-phosphate to yield myo-inositol. Previously, though the creation of an INO1 conditional double knockout cell line, it was demonstrated that the de novo synthesis of myo-inositol is essential to the survival of blood-stream form *Trypanosoma brucei* (*T. brucei*) [Martin and Smith 2006]. Although this paper described the conversion of glucose-6-phosphate to D-myo-inositol-3-phosphate, there is no teaching regarding the purification of D-myo-inositol-3-phosphate or indeed any suggestion that D-myo-inositol-3-phosphate could be of use in further chemical synthesis.

It is amongst the objects of the present invention to obviate and/or mitigate one or more of the aforementioned disadvantages.

SUMMARY OF INVENTION

The present invention is based in part on the provision of a purified and highly active INO1 enzyme from *T. brucei* and other organisms and its use to convert glucose-6-phospate or fructose-6-phosphate to D-myo-inositol-3-phosphate.

Thus, in a first aspect there is provided a method of preparing pure or substantially pure D-myo-inositol-3-phosphate or protected and/or derivative forms thereof, for use in further chemical reactions, comprising the steps of:

a) contacting the enzyme D-myo-inositol-3-phosphate synthase (INO1) with labeled or unlabeled, protected or unprotected glucose-6-phosphate and/or fructose-6-phosphate in order to generate labeled or unlabeled, protected or unprotected D-myo-inositol-3-phosphate; and b) optionally further reacting said labeled or unlabeled, protected or unprotected D-myo-inositol-3-phosphate with another enzyme or chemical to generate a further molecule; and c) purifying said labeled or unlabeled, protected or unprotected D-myo-inositol-3-phosphate or said further molecule.

A labeled form of glucose-6-phosphate or fructose-6-phosphate may include various radio or stable isotope labelled versions, and such labeled forms may be generated and/or obtained from commercial sources such as Sigma (Gillingham, Dorset, UK), CDN Isotopes (Pointe-Claire, Quebec, Canada) or ARC (St. Louis, Mo., USA).

A derivative of D-myo-inositol-3-phosphate is understood to mean a molecule which is derived from D-myo-inositol-3-phosphate following further chemical or enzymatic reaction. An example of this would be myo-inositol, which can be obtained from D-myo-inositol-3-phosphate by reaction with a further enzyme (see below).

The present invention by providing labeled or unlabeled, protected or unprotected D-myo-inositol-3-phosphate enables the production of further chemical moieties which may be of direct use or may be employed in further chemical synthesis. For example D-myo-inositol-3-phosphate can be converted by myo-inositol-monophosphate phosphatase (IMPase) to yield myo-inositol. One or more hydroxy functional groups on D-myo-inositol-3-phosphate or myo-inositol may easily be protected, before or after generation of the myo-inositol, so as to provide a protected compound suitable for use in further chemical synthesis. In this manner it is possible to readily synthesise various phosphatidylinositols (PIs), phosphatidylinositol phosphates (PIPs), inositol phosphates (IPs), glycosylphosphatidylinositol (GPI) and mytothiol.

Unexpectedly the present inventors have shown that fructose-6-phosphate and glucose-6-phosphate are both substrates for *T. brucei* INO1 (TbINO1) and are able to be fully converted to D-myo-inositol-3-phosphate, which, for example, simplifies subsequent purification of D-myo-inositol-3-phosphate. However, it is to be appreciated that other INO1 enzymes may also be used, particularly for the conversion of glucose-6-phosphate, such as various parasitic and yeast INO1 enzymes.

The method may comprise contacting labeled, unlabeled, protected and/or unprotected glucose-6-phosphate and/or fructose-6-phosphate or any combination or mixture thereof, with immobilized INO1. Thus, the method may comprise contacting a solution or composition comprising a single glucose-6-phosphate and/or fructose-6-phosphate based reagent with an INO1 enzyme, or with a solution or composition comprising more than one such reagent. Consequently, the method may comprise generating labeled, unlabeled, protected and/or unprotected D-myo-inositol-3-phosphate or any combination or mixture thereof. The method may also comprise optionally further reacting said labeled, unlabeled, protected and/or unprotected D-myo-inositol-3-phosphate with another enzyme or chemical to generate a further molecule or molecules; and purifying said labeled, unlabeled, protected and/or unprotected D-myo-inositol-3-phosphate or said further molecule(s).

Following conversion to labeled or unlabeled, protected or unprotected D-myo-inositol-3-phosphate, or following reaction with a further enzyme or other chemical means, any INO1 enzyme or other enzyme/proteinaceous material may simply be removed, for example, by centrifugation of the reaction mix through a size-exclusion membrane, to remove any enzyme/protein present (e.g. having a size exclusion cut off of for example, 2-10 KDa). The resulting filtrate may then be freeze-dried, for example, to remove water, yielding substantially pure labeled or unlabeled, protected or unprotected D-myo-inositol-3-phosphate or said further molecule. Alternatively, the product may be purified by chromatographic means, such as High pressure liquid chromatography (HPLC) or ion-exchange. Substantially pure is understood to mean at least 90%, 95%, 98%, 99%, 99.5% or higher purity product in terms of all proteinaceous material.

Purification may comprise separating the INO1 enzyme or any other enzyme/proteinaceous material from of the labeled, unlabeled, protected and/or unprotected D-myo-inositol-3-phosphate or said further molecule(s).

The method may comprise immobilizing the INO1 enzyme on a solid support. Immobilization of the enzyme on a solid support, such as a polymeric support, may facilitate separation of the INO1 enzyme from the solution comprising the labeled, unlabeled, protected and/or unprotected D-myo-inositol-3-phosphate product(s) (and, in some embodiments unreacted reagents, buffer solution etc).

A polymeric support may for example comprise a polyethylene glycol (PEG) polymer, agarose or an agarose-based polymer, such as Sepharose (Sepharose is a beaded, cross-linked form of agarose and is a trademark of GE Healthcare). The solid support may be selected for having a particular affinity for the enzyme. For example, a polymeric solid support may be surface functionalised with a moiety (e.g. a terminal cyanide or amide group) to which a target enzyme can be covalently bound.

More preferably, the target enzyme may be physically bound to the solid support (e.g. physisorbed to the solid support), so as to minimize or substantially eliminate the influence of surface-immobilization on the activity of immobilized enzymes. The inventors have found that the INO1 enzymes of the present invention comprise a polyhistidine motif, susceptible to binding to a "His-tag", or similar affinity tag, such as a surface-immobilized nickel or cobalt chelate. Accordingly, a suitable solid support may for example include a nickel or cobalt agarose (e.g. in the form of beads), such as Ni- or Co-Sepharose.

Following reaction, the immobilized INO1 may be separated from the solution comprising labeled, unlabeled, protected and/or unprotected D-myo-inositol-3-phosphate or said further molecule(s), and any further reagents, by filtration.

The method may comprise contacting labeled, unlabeled, protected and/or unprotected glucose-6-phosphate and/or fructose-6-phosphate with immobilized INO1 which is constrained in a reaction vessel. Accordingly, separation of the INO1 enzyme from the product(s) may comprise causing a solution comprising said product(s) to flow out of the reaction vessel.

Not only does immobilizing the INO1 in this way facilitate separation, but it enables the enzyme to be utilised several times while on the solid support and/or recovered and reused.

The method may comprise of preparing pure or substantially pure D-myo-inositol-3-phosphate and/or protected and/or derivative forms by way of a batch process, in which the reaction is conducted in a series of steps using all of the reagents required for each batch in the respective steps.

Alternatively, one or more steps of the method may be conducted as a flow process. For example, immobilized INO1 may be retained within a column (e.g. on a particulate solid support) and the method may comprise flowing reagents into and through the column (so as to contact the INO1 with labeled, unlabeled, protected and/or unprotected glucose-6-phosphate and/or fructose-6-phosphate), and flowing a solution comprising labeled, unlabeled, protected and/or unprotected D-myo-inositol-3-phosphate product(s) out of the column, to thereby separate the INO1 enzyme therefrom.

Conducting these steps as a flow process may facilitate an increased rate of conversion of the glucose-6-phosphate and/or fructose-6-phosphate reagent(s) and thus an increased amount of product(s) within a given period. For example, the conversion rate may be increased by 50%, or more than 50%, and may be increased by at least 60%, 75%, or 90%. The conversion rate may be increased in some instances by between around 80%-120%, or around between 90%-110%, or between around 95%-100%.

The method may comprise passing a solution through the column once, or more than once. For example, solution may be collected from the column and all or a portion of the solution may be re-introduced into the column.

Recycling all or a portion of the solution in this way may be desirable for example to increase the proportion of labeled/unlabeled/protected/unprotected glucose-6-phosphate and/or fructose-6-phosphate reagent which is converted into a corresponding D-myo-inositol-3-phosphate product.

Incomplete conversion may for example occur for certain reagents in combination with certain INO1 variants. A rate of flow through the column may lead to incomplete conversion, for example in order to maximize a rate of conversion. Thus multiple passes through the column may facilitate both an increased rate of conversion and an increased percentage of conversion of the reagents.

One or more further steps of the method may be conducted as a continuous flow process. Conveniently, for example, product(s) may be purified, i.e. separated from the solution collected from the column, using a continuous flow chromatographic method. Said continuous flow chromatographic method may comprise using a column, such as an HPLC or ion-exchange column.

The method may comprise immobilizing a further enzyme or chemical. Further reacting the said labeled or unlabeled, protected or unprotected D-myo-inositol-3-phosphate with another enzyme or chemical to generate a further molecule may comprise immobilizing the other enzyme or molecule, generally as described above, and contacting the labeled, unlabeled, protected and/or unprotected D-myo-inositol-3-phosphate product(s) therewith. Said further reaction(s) may be conducted as a batch or as a continuous flow process analogous to those described above.

In one embodiment, solution may be caused to flow into, through and out of a column comprising immobilized INO1 and subsequently into, through and out of a further column comprising immobilized further enzyme or other chemical. All or a portion of the solution may be caused to pass through each column once or more than once.

Advantageously, the present inventors have also found that through the use of suitable buffers, the buffer may also be removed through evaporation during freeze-drying. For example, a buffer such as ammonium bicarbonate (pH 8±0.5) decomposes to carbon dioxide, ammonia, and water vapor upon heating/freeze-drying. Advantageously, INO1 from *T. brucei* can be maintained and used in ammonium bicarbonate buffer, which facilitates the methodology described herein and subsequent purification of reaction products, as the buffer can easily be removed, yielding a purified product substantially free of salts. This can be particularly advantageous in further reactions, as the product can simply be reconstituted directly into a desired buffer or solvent of choice, for any subsequent use, including further chemical/enzymatic reaction.

The *T. brucei* INO1 enzyme is preferred and the enzyme may be obtained as described previously in Martin and Smith 2006. However, the enzyme may be further cloned into an appropriate expression vector, such as pET15b (Invitrogen) to allow overexpression of the enzyme (as described hereinafter). Other INO1 enzymes may not possess the high activity of the *T. brucei* INO1 enzyme, but through mutagenesis techniques, well known to the skilled reader, enzyme activity may be manipulated and increased. Once expressed, the enzyme may be purified by suitable chromatographic techniques, for example, as described in further detail herein and may preferably stored in a buffered solution, such as ammonium bicarbonate, which is thought to help stabilise and/or maintain enzyme activity. This buffer can also easily be removed, following enzyme conversion, as discussed above.

Preferably the conversion of glucose-6-phosphate or fructose-6-phosphate by the *T. brucei* INO1 enzyme is carried out in a buffered solution, most preferably an ammonia bicarbonate solution, buffered at between pH 7.5-8.5, such as pH 8. $NAD^+$ should also be present and optionally a reducing agent, such as dithiothreitol (DTT) and ammonium acetate. An exemplary enzyme reaction solution is 7.5-15 mM (such as 10 mM) ammonia bicarbonate (pH 8), 0.5-1.5 mM Nicotinamide adenine dinucleotide+ ($NAD^+$) (such as 1 mM); 0.5-1.5 mM, such as 1 mM DTT; and 1-5 mM, such as 2 mM $NH_4Ac$. As mentioned above the use of ammonium acetate may be advantageous, as ammonium ion may serve to stabilise the enzyme and moreover, the enzyme storage and reaction solution may be similar—thus simplifying the process.

It will be appreciated that in embodiments of the method comprising passing a solution through a column, the solution composition may vary along the column, as a reaction/reactions within the column proceeds. Moreover, where solution is recycled, the composition of fresh solution entering the column may differ from the recycled solution or from the mixture therebetween, formed within the column.

Conversion of D-myo-inositol-3-phosphate to myo-inositol may be carried out using IMPase, such as commercial bovine IMPase from Sigma (Gillingham, Dorset, UK). If one or more hydroxyl groups D-myo-inositol-3-phosphate is/are protected, the corresponding group in myo-inositol will also be protected. Thereafter protected or unprotected myo-inositol may be readily converted to other molecules using enzymes or chemical reactions known in the art.

Chemical manipulation of D-myo-inositol-3-phosphate, using known protection/deprotection chemistry to form useful appropriately protected enantiomeric pure inositol intermediates can easily be conducted.

For example, initial isopropylidene protecting group chemistry allowed the formation of the enantiomeric pure D-1,2-O-isopropylidene-3-phosphate-myo-inositol (1) in adequate yields (~70%).

Moreover upon the addition of a second equivalent, the second isopropylidene group prefers the 5,6-diol (2), this may be due interactions/influence of the phosphate at the 3-position. It may be possible that by masking the charge of the phosphate, as a tri-ester not only would this improve solubility in organic solvents, it may allow promote a higher proportion of the second isopropylidene group to the 4,5-diol (3). This would be a highly desirable intermediate, as de-phosphorylation with aqueous HF (4) and subsequent selective benzylation at the 3-position, forming the enantiomeric pure D-3-O-benzyl-1,2:4,5-di-O-isopropylidene-myo-inositol (5). This is the enantiomeric protected intermediate that has been used in retrosynthetic strategies of mycothiol, PIPs, IPs and several GPI anchor intermediates. (3, 4, 5).

Alternative protection may be envisaged using, for example, 1-ethoxycyclohexene, i.e. cyclohexylidene groups, as well as protecting (masking) the phosphate prior to [See below] protecting the hydroxyls. This may allow more efficient formation of di-isopropylidene or di-cyclohexylidene protection.

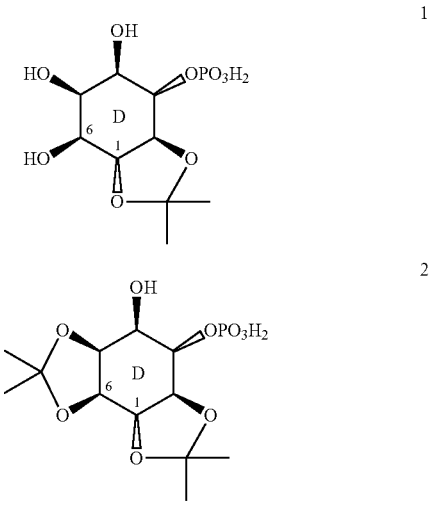

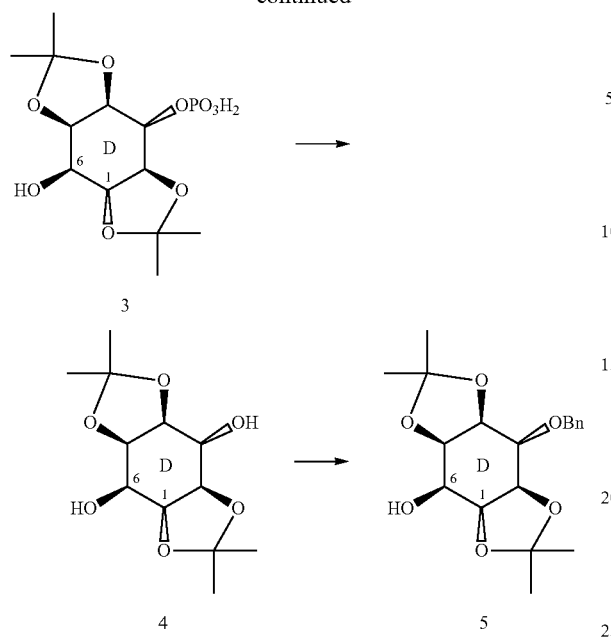

Other synthetic routes starting from either enantiomeric pure D-3-phosphate myoinositol or the D-1,2-O-isopropylidene-3-phosphate-myo-inositol (1) or the D-1,2:5,6-di-O-isopropylidene-3-phosphate-myo-inositol (2) are known to the skilled addressee.

For example the D-1,2-O-isopropylidene-3-phosphate-myo-inositol (1) can be regioselectively modified at the one-position with an allyl group using dibutyltin oxide chemistry. Subsequent removal of the phosphate group and benzylation of the 3, 4 and 5-positions affords the very useful D-1,2-O-isopropylidene-3,4,5-tri-O-benzyl-6-O-allyl-myo-inositol (6), which is commonly used in GPI anchor synthesis [Cottaz et al. 1995, Crossman et al 1999, Crossman et al 2005, Borissow et al. 2001].

Alternatively the non-natural L-isomer myo-isomer for mycothiol analogues are easily accessible form D-3-phosphate-myo-inositol, upon peracetylation and removal of the phosphate by aqueous HF. This affords D-1,2,4,5,6-penta-O-acetyl-myo-inositol (7), also known as L-2,3,4,5,6-penta-O-acetyl-myo-inositol (7), (as the D-3-hydroxyl is equivalent to the L-1-hydroxyl) which is ready for coupling to the activated protected sugar [Lee and Rosazza 2004].

Various selective protection/deprotection reactions to form useful inositol intermediates are shown in Schemes A-E.

The protection/deprotection chemistries described below are know in the art and are described widely, for example in the review, "Chemistry of Inositol Lipid Mediated Cellular Signaling", Potter and Lampe, Angew. Chem. Int. Engl., 1995, 34, 1933-1972. Protection/deprotection chemistries of inositol, or which are applicable to inositol and related materials, are also described in references [10-26] listed below.

For the avoidance of doubt, D-myo-inositol-3-phosphate may alternatively be given the systematic chemical name L-myo-inositol-1-phosphate and thus the nomenclatures are interchangeable.

Scheme A—Selective Phosphate Benzylation Followed be Peracetylation and Removal of Phosphate

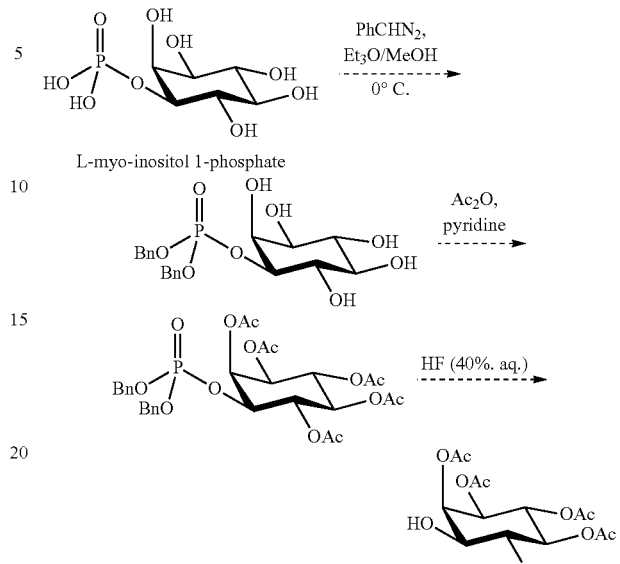

Scheme B—Selective Phosphate Protection to Provide Intermediates with Improved Solubility in Organic Solvents

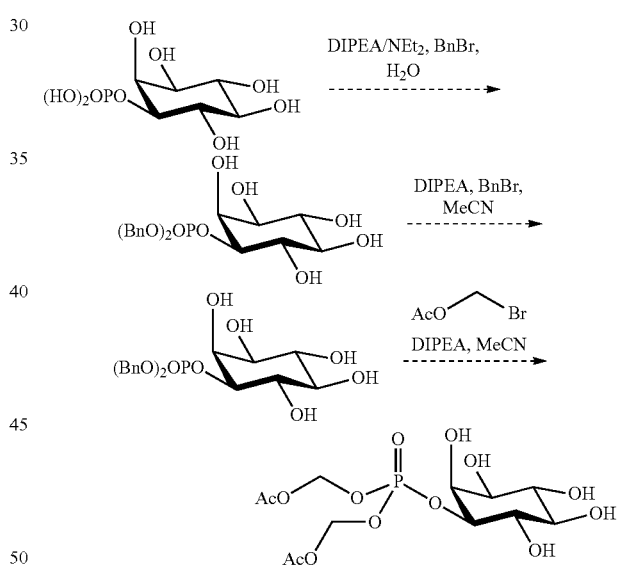

Scheme C—Global Protection of Hydroxyl Groups by Benylation or Acetlyation

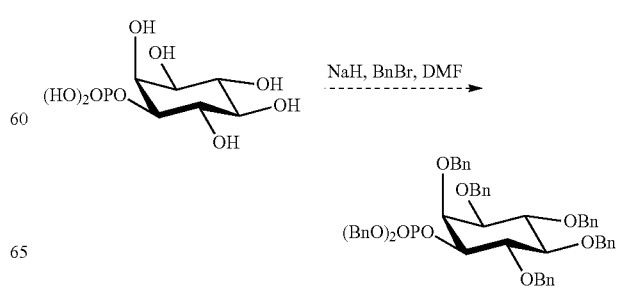

-continued

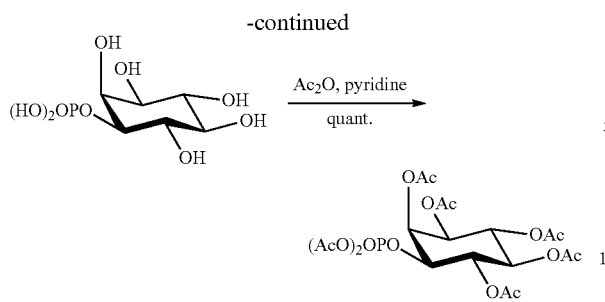

Scheme D—Dephosphorylation

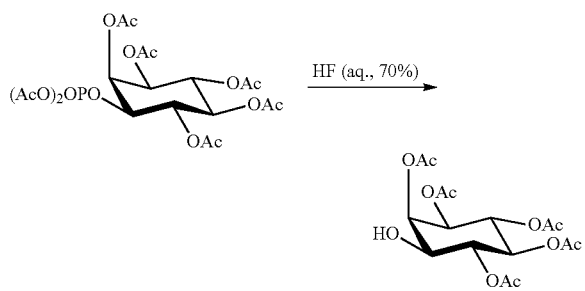

Scheme E—Dephosphorylation by Acid Phosphatase

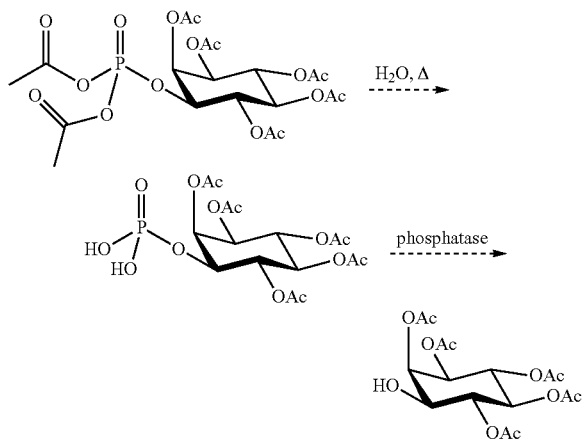

The possibility of using the methodologies described herein to form biologically relevant labelled myo-inositol containing molecules, will allow new avenues of research as these reagents/tools are presently propitiatory expensive or just not available. The use of commercial hexakinase to form labelled glucose-6-phosphate could be subsequently used in the INO1 biotransformation to form labelled D-myo-inositol-3-phosphate. This labelled product could be dephosphorylated to afford labelled inositol, or utilised in protection chemistry steps that will be optimised by this proposal for a wide range of labelled inositol containing molecules.

DETAILED DESCRIPTION

The present invention will now be further described by way of example and with reference to the figures which show:

FIG. 1: shows structures of important biomolecules containing myo-inositol.

FIG. 2: shows the expression and purification of recombinant TbINO1: (A) TbINO1 was cloned into the expression vector pET 15b (N-terminal Hexa-His tag) and transformed into Rosetta competent cells, and grown, expressed and purified as described in experimental procedures. TbINO1 protein samples from each purification step were separated on a 10% SDS-PAGE gel and stained with Coomassie brilliant blue. Lane 1, cleared lysate; Lane 2, unbound to $Ni^{2+}$ column; Lane 3, washed column, Lane 4, pooled elutions from $Ni^{2+}$ column; Lane 5, pooled elution from Hi-Trap Blue Sepharose. (B) Purified recombinant TbINO1 was passed through a high-resolution gel-filtration Sephacryl S-300 column. Absorbance at 280 nm was monitored against elution volume. The column was calibrated with globular protein standards (Biorad).

FIG. 3: shows the separation of reaction products from TbINO1 assay by Dionex HPLC. Panel A shows separation of reaction products from standard assay using glucose-6-phosphate as substrate (i), with elution at identical times as standards of inositol-1-phosphate (ii), glucose-6-phosphate (iii) and fructose-6-phosphate (iv). Panel B shows separation of reaction products from assay mixture using fructose-6-phosphate as substrate at various time points.

Figure 4:
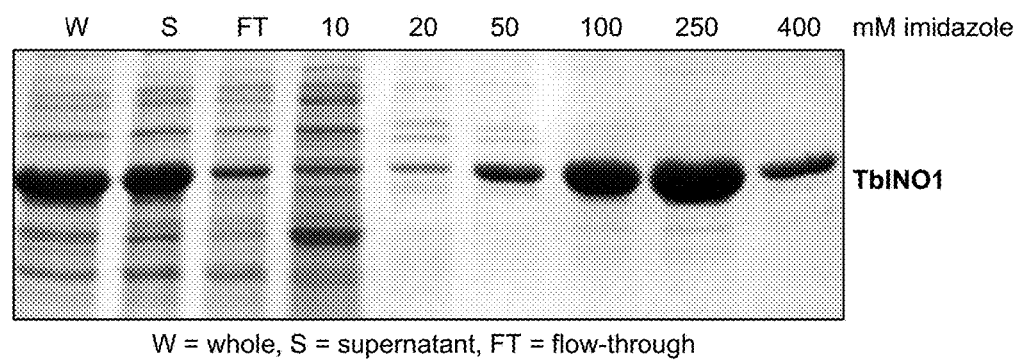

FIG. 4 shows the expression and purification of surface immobilized recombinant TbINO1 on Ni Sepharose: (A) TbINO1 was cloned into the expression vector pET 15b (N-terminal Hexa-His tag) and transformed into Rosetta competent cells, and grown, expressed and purified as described in experimental procedures. TbINO1 protein samples from each purification step were separated on a 10% SDS-PAGE gel and stained with Coomassie brilliant blue. Protein gel from typical TbINO1 affinity chromatography purification. W=whole cell, S=supernatant, FT=flow through, elution's of 10, 20, 50, 100, 250 and 400=concentration of imidazole in mM.

Figure 5:
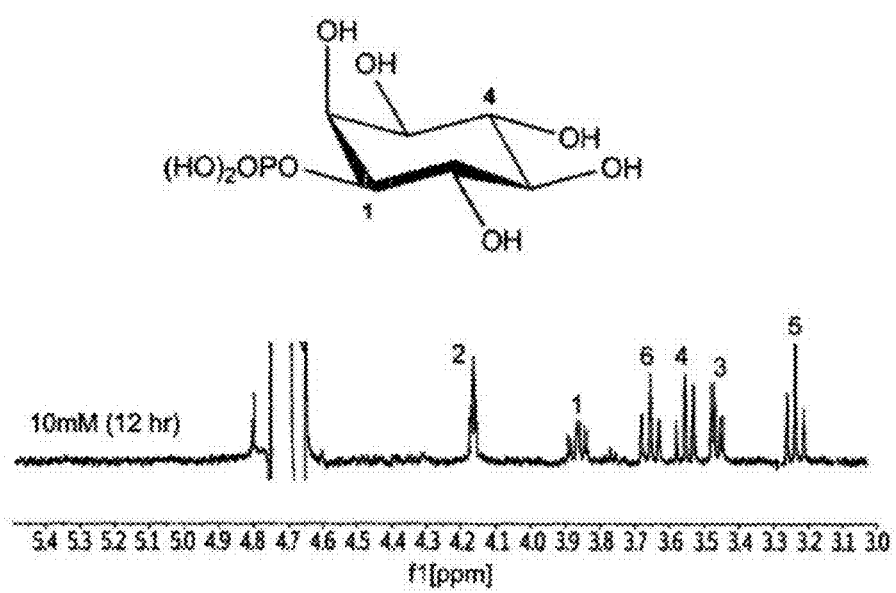

FIG. 5 shows a 400 MHz $^1H$ NMR spectra in $D_2O$ of D-myo-inositol-3-phosphate product obtained after a 12 hour period of 10 mM D-glucose 6-phosphate, 2 mM $NAD^+$, 1 mM 2-mercaptoethanol and 50 mM ammonium bicarbonate (pH 8.5) solution passed through a 5 mL Ni-Sepharose TbINO1 affinity column, prepared as described herein. The spectrum has been annotated to indicate which proton signals have been assigned to the corresponding adjacent C1-C6 carbons, numbered as shown in the representation shown above the spectrum).

MATERIALS AND METHODS

Cloning The TbINO1 was PCR amplified from TbINO1-pBAD (described previously {Martin, 2006 #113}) using the primers 5'-CTCGAGATGCCAGCCGTCCGTACG-3' and 5'-GGATCCTCAACTTCCCACGCCGCC-3' containing XhoI and BamHI restriction sites respectively (underlined in primer sequences). The purified PCR product was digested with XhoI and BamHI and ligated into pET15b (Invitrogen) via the same restriction sites and sequenced.

Site Directed Mutagenesis

Site directed mutagenesis was performed using a Quick-Change kit (Stratagene) according to manufacturers' instructions with TbINO1-pET15b as the template and sequenced to confirm presence of desired mutation. The pair of complementary primers to mutate the selected amino acids of TbINO1 to alanine are as follows:

K305A:
5'-GTTGTTGGGGATGACTTTGCaAGTGGTCAAACAAAGG-3'
and

5'-CCTTTGTTTGACCACTtGCAAAGTCATCCCCAACAAC-3';

D339A:
5'-ATCTTGGCAATAATGcCGGATATAACTTGGCAGC-3'
and

5'-GCTGCCAAGTTATATCCGgCATTATTGCCAAGAT-3';

K353A:
5'-CCCCAAAGCAGTTTCGTTCGGCGGAGGTTACGAAAGGCGGTGT-3'
and

5'-ACACCGCCTTTCGTAACCTCCGCCGAACGAAACTGCTTTGGGG-3';

K357A:
5'-CGTTCGAAGGAGGTTACGGCAGGCGGTGTGCTGGACGATATGG-3'
and

5'-CCATATCGTCCAGCACACCGCCTGCCGTAACCTCCTTCGAACG-3';

K395A:
5'-CTCCCGTATGTGGGTGACAGCGCACGTGCATTGGATGAGTACA-3'
and

5'-TGTACTCATCCAATGCACGTGCGCTGTCACCCACATACGGGAG-3';

D421A:
5'-GGTGCTCCATAACACATGCCAGGCCTCGTTGCTGGCTGCACCACT-3'
and

5'-AGTGGTGCAGCCAGCAACGAGGCCTGGCATGTGTTATGGAGCACC-3';

K477A:
5'-ACTTTTATCTTACTTGCTGGCGGCTCCACGTGTGCCGGAG-3'
and

5'-CTCCGGCACACGTGGAGCCGCCAGCAAGTAAGATAAAAGT-3'.

Protein Over Expression and Purification

The over expression construct of interest was freshly transformed into BL21 Rosetta (DE3) cells (Invitrogen). A single colony was used to inoculate LB-Amp broth and the cells were grown at 37° C. with shaking until the OD (600 nm) was approximately 0.6. Protein expression was induced by the addition of 1 mM IPTG, and the cells were grown further 16 hrs at room temperature.

TbINO1 has been over-expressed using the expression plasmid pET15b (Invitrogen), which has increased the yield of recombinant protein from approximately 2 mg/L to 20 mg/L. TbINO1 was highly purified via a three step purification protocol using Ni-NTA affinity, HiTrap Blue sepharose affinity and size exclusion chromatography.

Small-scale protein purification of ScINO1 and the various site directed mutated TbINO1 were performed according to Martin and Smith unpublished.

For larger scale purification of wild type TbINO1 for biochemical characterisation, the cells were suspended in buffer A (20 mM Tris pH 7.5, 250 mM NaCl, 50 mM imidazole, 3 mM 2-mercarptoethanol) and lysed using a one-shot cell disrupter (Constant Systems) at a pressure of 30 000 Psi. Insoluble protein and cell debris was collected by centrifugation (50 000 g, 30 min 4° C.). The resulting supernatant was loaded onto a Hi-Trap Chelating Sepharose HP column (Amersham) which was pre-equilibrated with buffer A. Protein was eluted with a linear gradient of 0-100% buffer B (1.6 M imidazole) with TbINO1 elution with approximately 25% buffer B (400 mM imidazole). Fractions were chosen based on purity determined by SDS-PAGE analysis and dialysed extensively against buffer C (20 mM Tris pH 7.5, 50 mM NaCl and 3 mM 2-mercaptoethanol) using Snakeskin dialysis tubing (Pierce) with a MWCO of 10 KDa. The dialysed sample was then applied to a Hi-Trap Blue Sepharose column (Amersham) which had been pre-equilibrated with buffer C. Protein was eluted with a line gradient of 0-100% buffer D (2M NaCl). One pool of TbINO1 was found to elute from the column prior to the NaCl gradient, a second pool of TbINO1 eluted with approximately 1.25M NaCl. Each pool was dialysed separately against buffer E (20 mM Tris pH7.5, 50 mM NaCl and 5 mM DTT) prior to concentration to approximately 80 mg/mL using centrifugal concentrators (MWCO 30 KDa, Vivaspin). The concentrated protein was then loaded onto a Superdex 200 column (Amersham) which had been pre-equilibrated with buffer E and eluted with the same buffer. Fractions from this size elusion chromatography were chosen conservatively from the centre of the protein peak.

The purity of TbINO1 was confirmed firstly by SDS-PAGE (FIG. 1a) and secondly by MALDI-TOF/MS analysis (FIG. 1b), both methods showed the recombinant protein to have a molecular size of approximately 60 kDa, which is in good agreement with the predicted size of 59.2 kDa. A secondary peak is present on the MALDI-TOF/MS spectrum which corresponds to the doubly protonated species with a molecular weight of 30.4 kDa. Size elusion chromatography data showed that in its native state TbINO1 predominantly exists as a tetramer (FIG. 1c), which is supported by data from analytical ultra centrifugation (FIG. 1d).

Synthesis of Glucose-6-Phosphte Analogues

Various glucose analogues (10-45 mg) were dissolved in 1 ml of Tris.HCl (100 mM, pH 8.0) long with ATP (100 mM) and $MgCl_2$ (50 mM), Yeast hexokinase (100 units) was added and incubated at 30° C. overnight. The reaction mixture is passed through a 5×1 cm column of Dowex (AG1, borate form) to bind excess phosphate and eluted with a gradient of borate, followed by a 3×1 cm column of AG50W×8 ($H^+$) to form the free acid. Eluted products were freeze-dried and checked by ES-MS prior to phosphate quantification by acid phosphatase treatment followed by malachite green analysis.

The following compound were prepared galactose-6-phosphate, 2-fluoro-glucose-6-phospahte, 3-fluoro-glucose-6-phospahte, 4-fluoro-glucose-6-phospahte, 3-O-methyl-glucose-6-phospahte and glucose-1-O-methyl-6-phospahte.

Enzyme Assays

Conversion of Glucose-6-Phosphate to D-Inositol-3-Phosphate

An assay to test the glucose-6-phosphate isomerase activity of TbINO1 was performed using a coupled assay with inositol-3-phosphate monophosphatase (IMPase, available from Sigma).

Glucose-6-phosphate is isomerised into D-inositol-3-phosphate by the action of TbINO1. The reaction is monitored by following the concentration of phosphate from the formed inositol-3-phosphate (not glucose-6-pbosphate) which can be cleaved by IMPase to leave myo-inositol and free phosphate. The concentration of phosphate released can then detected colormetrically by Biomol (malachite) green by measuring absorbance at 620 nm.

Therefore the amount of inositol-3-phosphate formed from glucose-6-phosphate can be monitored.

Typical Glucose-6-Phosphate to Inositol-3-Phosphate Reaction

| Components (50 mL) |
| --- |
| 10 mM Ammonia bicarbonate (pH ~8) |
| Glucose-6-phosphate (100 mg) |
| 1 mM NAD+ |
| 1 mM DTT |
| 2 mM NH$_4$Ac |
| 50 µg TbINO1 |

The reaction was incubated overnight at 37° C.

A portion of the reaction (10 ul) was removed and the reaction stopped by heating to 100° C. for ten minutes.

The IMPase assay was then performed on this small aliquot to ensure all the glucose-6-phosphate had been isomerised into inositol-3-phosphate, i.e. gone to completition.

Typical IMPase Assay

The IMPase part of the coupled assay was tested first in order to verify the commercially bought IMPase activity and obtain a standard curve for phosphate detection. The assay was run in a clear 96 well plate with 50 µL of reaction mixture in each well with the following constituents with either inositol-phosphate or free phosphate as the substrate:

| Final Concentration | Stock | Vol. Per 50 µL |
| --- | --- | --- |
| 50 mM Tris. pH 8.0 | 0.5M | 5 µL |
| 5 mM MgCl$_2$ | 0.2M | 1.25 µL |
| INO1 Reaction mixture | | 0.5 µL |
| 1 mM DTT | 100 mM | 0.5 µL |
| IMPase 0.5 µgml$^{-1}$ | In 50 mM Tris pH 7.5 + 20% glycerol | 2 µL |
| Water | | 40.75 µL |

The reaction was started by adding IMPase to each well last and once added the plate was incubated for 1 hour at 37° C. The reaction was stopped by heating to 100° C. for 10 minutes, followed by the addition of biomol (malachite) green (100 µL). The plate was incubated at room temperature for 20 minutes and then the absorbance at 620 nm was read using a spectrophotometer.

A control with IMPase replaced with water was used to account for any free phosphate contained in the reaction mixture. The phosphate standard curve was formulated using free phosphate as the substrate and this standard curve was used to calculate the amount of inositol-1-phosphate cleaved by the IMPase.

Work Up of Inositol-3-Phosphate Product.

The final product (inositol-3-phosphate) was obtained from the reaction mixture by first removing the protein from the reaction mixture by centrifugation with a protein membrane (10 kDa molecular weight cut off) and then an overnight freeze-drying to remove the water and the ammonium acetate buffer (which evolves as ammonia, carbon dioxide and water), yielding essentially pure inositol-3-phosphate.

Alternative Direct Assay

An alternative reaction mixture consisted of 2 mM Tris-Ac (pH 9), 2 mM glucose-6-phosphate, 1 mM NAD$^+$, 1 mM DTT, 2 mM NH$_4$Ac and 5 µg protein in a final volume of 20 µL. The reaction was incubated at 37° C. for 1 hr and terminated by heating at 100° C. for 10 min and the addition of 80 µL of 10 mM NaOH. For inhibitor studies the standard reaction mixture was prepared without glucose-6-phosphate, the inhibitor was added to the reaction and incubated on ice for 10 min prior to the addition of glucose-6-phosphate and subsequent incubation of 37° C. for 1 hr.

After quenching the reaction mix was analysed by high performance anion-exchange chromatography using a Dionex HPLC system with a CarboPacPA-1 column and PA-1 guard column (Dionex). The column was pre-equilibrated with 95% Buffer A (1 mM sodium hydroxide) and 5% Buffer B (1M sodium acetate+1 mM sodium hydroxide). An aliquot (20 µL) of the quenched reaction mixture was injected onto the column and eluted a linear gradient of 5-40% buffer A, detected with pulsed amperometric detection and analysed with Chromeleon software (Dionex). The substrate glucose-6-phosphate and the product inositol-3-phosphate are clearly separated by this method.

Glucose-6-Phosphate Isomerase (PGI) Activity by TbINO1

Figure 2A:
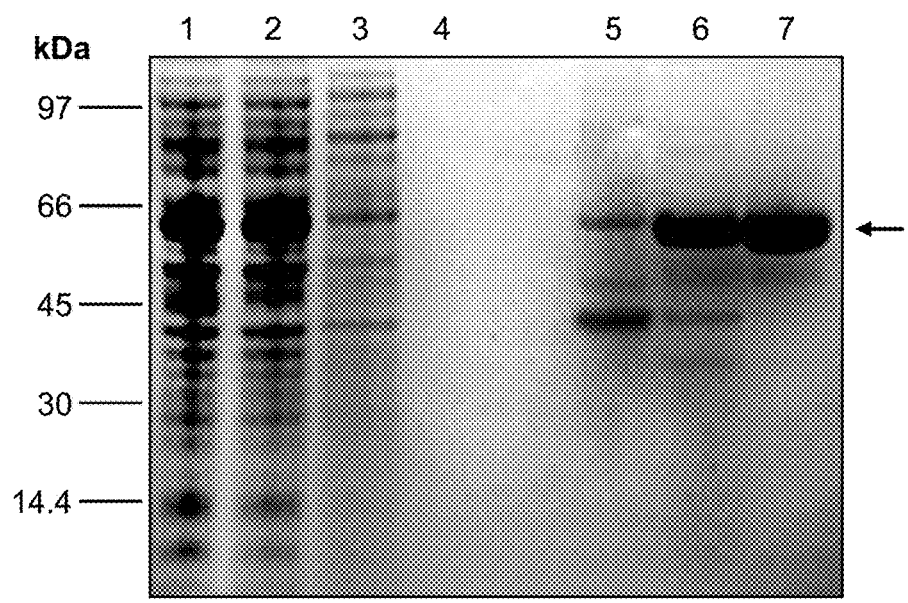

Previously preliminary biochemical characterisation of TbINO1 was performed using a coupled assay with a commercial inositol-3-phosphate monophosphatase (IMPase, as described above) and detection of the release of free phosphate by colorimetric analysis (Martin and Smith 2006). However, to overcome the disadvantages of using this assay system, in particular the potential inhibition of the IMPase and the high levels of free phosphate in some inhibitors to be tested, it was decided to employ high performance ion-exchange chromatography to quantify enzyme activity (described above). Using this method glucose-6-phosphate and inositol-3-phosphate were successfully separated from each other, as well as from other components of the reaction mixture (FIG. 2a). An additional peak was observed in the traces from enzyme assays, which was not present in the control reactions (enzyme and substrate blanks) (FIG. 2a), suggesting that the unidentified peak was a result of catalysis by TbINO1. This unidentified peak had an identical elution time as fructose-6-phosphate, suggesting that in the standard reaction mixture with glucose-6-phosphate as the substrate, TbINO1 was able to form fructose-6-phosphate in addition to inositol-3-phosphate.

Fructose-6-phoshate was tested as a substrate in the standard reaction mixture, peaks with identical elution times to fructose-6-phosphate, glucose-6-phosphate and inositol-3-phosphate standards respectively, were observed (FIG. 2b). When the reaction was allowed to proceed for longer time periods only inositol-3-phosphate was observed (FIG. 2b), showing the quantitative conversion of fructose-6-phosphate to inositol-3-phosphate with an intermediate conversion to glucose-6-phosphate. The production of myo-inositol-3-phosphate from fructose-6-phospahte was confirmed two-fold, firstly the presence of myo-inositol was confirmed by GC-MS analysis after acid hydrolysis, and secondly this was shown to be inositol-3-phosphate, as it was used as a substrate for bovine IMPase (data not shown). The production of glucose-6-phosphate from fructose-6-phosphate was established using a traditional assay for glucose-6-phosphate isomerase activity, via a coupled assay with glucose dehydrogenase.

Alternative Glucose-6-Phosphate Isomerase Assay

Glucose-6-phosphate isomerase activity was measured using the coupled assay described previously [Gracy and Tilley 1975]. The standard assay mixture contained 0.1 mM Tris-HCl (pH 9), 2 mM EDTA, 0.5 mM β-NADP$^+$, 1 mM fructose-6-phosphate, 1 U glucose-6-phosphate dehydrogenase (Type XV from bakers yeast, Sigma) and 100 µg recombinant protein. Enzyme activity was measured as an increase in absorbance at 340 nm. One unit of activity is defined as 1 µmoles of β-NADP$^+$ reduced per minute under the assay conditions.

Site Directed Mutagenesis of TbINO1

Using the crystal structure of the *Archaeolglobus fulgidus* (Af) INO1 and associated site directed mutagenesis data, as well as the crystal structure of the *Saccharomyces cerevisiae* INO1, a series of TbINO1 mutants were generated, overexpressed in *E. coli* and purified using Ni-NTA beads, expression levels of all the mutant proteins was approximately the same as wild type TbINO1. After purification the mutated recombinant protein was tested for activity using the standard reaction mixture using either glucose-6-phosphate or fructose-6-phosphate as the substrate and the reaction products separated and quantified by HPLC as described previously.

With the exception of the TbK353A mutant, all the TbINO1 mutations resulted in the complete abolishment of the INO1 activity while retaining normal glucose-6-phosphate isomerase activity. The K353A mutant resulted in a decrease of INO1 activity to approximately 10%, whilst retaining all glucose-6-phosphate isomerase activity. It was not surprisingly that mutant K353A lost INO1 activity whilst retaining glucose-6-phosphate activity as the corresponding AfINO1 mutant was unable to bind $NAD^+$ which is essential for INO1 activity but not required for glucose-6-phosphate isomerase activity. However, the INO1 activity was not completely abolished in TbK353A suggesting that there may be weak binding of the $NAD^+$ still occurring.

AfD332 was suggested to be a ligand for the second metal ion required for catalysis and AfK306 is thought to work in with AfD332 aiding in this interaction, and therefore the mutation of this residues resulted in the loss of activity as AfINO1 has a requirement for metal ions for activity. However, TbINO1 does not require this metal ion for catalysis, but surprisingly mutation of the corresponding amino acids K421A and K395A in TbINO1 resulted in the total loss of INO1 activity, suggesting that in TbINO1 these residues has another essential roles for INO1 activity. However, mutation of these residues had no effect on the PGI activity, suggesting that they do not play crucial roles in PGI activity.

Mutant AfK367A displayed no glucose-6-phosphate binding and therefore was inactive. Likewise the corresponding mutant in TbINO1, K477A was inactive. However, this mutant still displayed glucose-6-phosphate isomerase activity. Suggesting either that there is a secondary active site on the protein for glucose-6-phosphate isomerase activity, or that glucose-6-phosphate is still binding to the protein, but the mutation is disrupting something else that is essential to the INO1 activity.

Inhibitors of Enzyme Activity

All compounds listed in Tables 2 and 3 were tested as potential substrates for TbINO1 in the standard reaction mixture and the reaction products separated by HPLC. However, no reaction products were observed for any of the compounds tested showing that TbINO1 has a strict substrate specificity for glucose-6-phosphate and fructose-6-phosphate. These compounds were then tested for their ability to inhibit the TbINO1 PGI or INO1 activity.

The TbINO1 was pre-incubated with potential inhibitor prior to the addition of glucose-6-phosphate or fructose-6-phosphate and quantification of inositol-3-phosphate and fructose-6-phosphate by HPLC. A number of glucose-6-phosphate analogues were generated, and these in addition to commercially available phosphorylated sugars were tested and the results shown in Table 2. Substitution of the 2-position of glucose-6-phosphate resulted in an inhibitor of both INO1 and PGI activity, interestingly substitution with fluoro- was more potent than the deoxy-derivative. There was no inhibition observed with a substitution in the 2-position of a non-phosphorylated glucose, indicating that phosphorylation is important for inhibition. Substitution in the 3 and 1-positions also resulted in inhibition of both INO1 and PGI activities. No inhibition of INO1 or PGI activities were observed in the presence of glucose-1-phosphate, glycerophosphate, 6-phosphogluconic acid, acetylglucosamine-1-phosphate, acetylglucosamine-6-phosphate, mannose-6-phosphate and galactose-6-phosphate.

A number of metabolic intermediates were also tested as potential inhibitors against INO1 and PGI activity, the results are shown in Table 3. Inhibition was observed by GAP, OAA, DHAP against both INO1 and glucose-6-phosphate isomerase activity. Interestingly no inhibition was observed due the presence of the non-phosphorylated counterparts of GAP and DHAP, glyceraldehyde and DHA respectively, suggesting that the phosphate group is essential for efficient binding. No inhibition was observed in the presence of PEP, pyruvate or VPA.

Tables

TABLE 1

Site directed mutagenesis of TbINO1. Proposed catalytic residues of TbINO1 were mutated using a Quickchange mutagenesis kit (Stratagene). Mutated recombinant protein was expressed in *E. coli*, purified by Ni-NTA chromatography and tested for INO1 and PGI activity using glucose-6-phosphate and fructose-6-phosphate as substrates respectively. Reaction products were separated using a Dionex HPLC system with pulsed amperometric detection.

|  | Substrate Glucose-6-P | | Substrate fructose-6-P | |
| --- | --- | --- | --- | --- |
| TbINO1 mutant | Ino-3-P produced | Fructose-1-P produced | Ino-3-P produced | Glucose-6-P produced |
| K306A | No | Normal | No | Normal |
| D340A | No | Normal | No | Normal |
| K353A | <10% of normal | Normal | <10% of normal | Normal |
| K357A | No | Normal | No | Normal |
| K395A | No | Normal | No | Normal |
| D421A | No | Normal | No | Normal |
| K477A | No | Normal | No | Normal |

TABLE 2

Glucose-6-phosphate analogues and phosphorylated sugars as inhibitors of TbINO1. Potential inhibitors were pre-incubated with recombinant TbINO1 prior to determination of either INO1 or PGI activities using glucose-6-phosphate or fructose-6-phosphate as the substrate respectively. Reaction products were separated using a Dionex HPLC system with pulsed amperometric detection and IC50 determined.

| Inhibitor | IC50 INO1 activity (mM) | IC50 PGI activity (mM) |
| --- | --- | --- |
| 2-Deoxyglucose-6-P | 4 | 4 |
| 2-Deoxyglucose | >10 | >10 |
| 2-F-Glucose-6-P | 1 | 1 |
| 3-OMe-Glucose-6-P | 2.5 | 3 |
| 1-OMe-Glucose-6-P | 2.5 | 2.5 |
| 4-F-Glucose-6-P | >10 | >10 |
| 3-F-Glucose-6-P | 2.5 | 2.5 |
| Glucose-1-P | >10 | >10 |
| Glycerophosphate | >10 | >10 |
| 6-phosphogluconic acid | >10 | >10 |
| Acetylglucosamine-1-P | >10 | >10 |
| Acetylglucosamine-6-P | >10 | >10 |
| Mannose-6-P | >10 | >10 |
| Galactose-6-P | >10 | >10 |

TABLE 3

Metabolic intermediates as inhibitors of TbINO1. Potential inhibitors were pre-incubated with recombinant TbINO1 prior to determination of either INO1 or PGI activities using glucose-6-phosphate or fructose-6-phosphate as the substrate respectively. Reaction products were separated using a Dionex HPLC system with pulsed amperometric detection and IC50 determined.

| Inhibitor | IC50 INO1 activity (mM) | IC50 PGI activity (mM) |
|---|---|---|
| GAP | 2 | 2 |
| Glyceraldehyde | >10 | >10 |
| OAA | 1.5 | 2 |
| DHAP | 3 | 3 |
| DHA | >10 | >10 |
| PEP | >10 | >10 |
| Pyruvate | >10 | >10 |
| VPA | >10 | >10 |

Continuous Flow Methods

An affinity column of immobilized TbINO1 was prepared as follows. Lysed *E. coli* was filtered and loaded onto a $Ni^{2+}$ Sepharose column, generally as described above (in the section entitled, "Protein over expression and purification"). Loading was in the amount of 40 mg proteinaceous material per mL of resin beads. The column was then washed with a buffer solution of (i) 10 mM imidazole (ii) 50 mM ammonium bicarbonate (at pH 8.5) (iii) 250 mM sodium chloride. Subsequently a further wash with 50 mM ammonium bicarbonate solution was conducted.

The purity of the immobilized TbINO1 was confirmed by SDS-PAGE (FIG. 4).

Referring now to Scheme 1, below, columns of capacity 1 mL and 5 mL were prepared.

4 mM, 10 mM and 20 mM D-glucose 6-phospate solutions (in an $NAD^+$, 2-mercaptoethanol, ammonium carbonate buffer solution; (pH 8.5) were prepared, as described above.

The 4 mM D-glucose 6-phospage solution was passed through the 1 mL column at a flow rate of 2.5 mL/hr for 12 hours.

The 10 mM and 20 mM solution were each passed through the 5 mL column at the same flow rate and for the same period.

The temperature of each column was maintained at 37° C. throughout.

Scheme 1

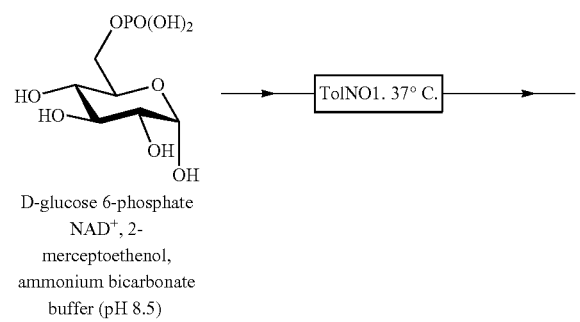

D-glucose 6-phosphate
$NAD^+$, 2-merceptoethenol,
ammonium bicarbonate
buffer (pH 8.5)

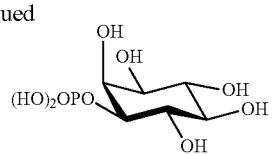

L-myo-inositol 1-phosphate
$NAD^+$, 2-merceptoethenol,
ammonium bicarbonate
buffer (pH 8.5)

Following purification by freeze-drying (to remove the ammonium carbonate), 42 mg of inositol-3-phosphate (Ino3P) product was obtained from the 4 mM Glc-6P solution passed through the 1 mL column. The highest yield (~100%) from the 5 mL column, of 210 mg Ino3P, was obtained was obtained using the 20 mM Glc-6P solution.

NMR spectra of the purified Ino 3P product were obtained and assigned and are consistent with high percentage conversion of the Glc-6P reagent into an enantiometrically pure product. An example spectrum (obtained from the 10 mM Glc-6P solution) is shown in FIG. 5.

These initial results demonstrate the utility of the method for preparing large amounts of enantiomerically pure D-Ino3P (i.e. L-Ino1P) using a continuous flow process. In addition, the high yield from the 20 mM Glc-6P solution demonstrates how the use of an affinity column facilitates re-use of the immobilized INO1 enzyme.

REFERENCES

1. Potter, B., and Lampe, D. (1995) Chemistry of inositol mediated cell signalling Angew Chem Int 34: 1933-1972
2. Cottaz, S., Brimacombe J. S, and Ferguson, M. A. J., Parasite glycoconjugates. Part 3. Synthesis of substrate analogues of early intermediates in the biosynthetic pathway of glycosylphosphatidylinositol membrane anchors J. Chem. Soc., Perkin Trans. 1, 1995, 1673-1678
3. Tegge W, Ballou C E. Chiral synthesis of D- and L-myo-inositol 1,4,5-trisphosphate Proc Natl Acad Sci USA. 1989 January; 86(1):94-8.
4. Martin, K. L. and T. K. Smith, 2006 *The glycosylphosphatidylinositol (GPI) biosynthetic pathway of bloodstream-form Trypanosoma brucei is dependent on the de novo synthesis of inositol.* Mol Microbiol. 61(1): p. 89-105.
5. Crossman, A., Brimacombe, J. S. and Ferguson, M. A. J., Smith, T. K., (1999), Synthesis of some second-generation substrate analogues of early intermediates in the biosynthetic pathway of glycosylphosphatidylinositol membrane anchors. Carbohydr. Res. 321, 42-51.
6. Crossman, A., Smith, T. K. Ferguson, M. A. J. and Brimacombe, J. S. (2005) Synthesis of a cell-permeable analogue of a glycosylphosphatidylinositol (GPI) intermediate that is toxic to the living bloodstream form of *Trypanosoma brucei*. Tetrahedron Letters. 46: 7419-7421.
7. Borissow, C. N., Smith, T. K., Ferguson, M. A. J, Brimacombe, J. S. (2001) Synthesis of 3'-, 4'- and 6'-deoxy and other analogues of D-glucosaminyl-phosphatidylinositol Tetrahedron Lett. 42, 121-123.
8. Lee, S. and Rosazza, J. (2004) First total synthesis of mycothiol and Mycothiol disulfide. Org Lett 6(3): 365-368.

9. Gracy, R. W., and B. E. Tilley. 1975. Phosphoglucose isomerase of human erythrocytes and cardiac tissue. Methods Enzymol. 4 1 [B]: 392-400.
10. Patel, M. P.; Blanchard, J. S., *J. Am. Chem. Soc.* 1998, 120, 11538-11539.
11. Rawat, M.; Av-Gay, Y., *FEMS Microbiol. Rev.* 2007, 31, 278-292.
12. Newton, G. L.; Fahey, R. C.; Cohen, G.; Aharonowitz, Y., *J. Bact.* 1993, 175, 2734-2742.
13. Fahey, R. C., *Ann. Rev. Microbiol.* 2001, 55, 333-356.
14. Sakuda, S.; Zhou, Z.-Y.; Yamada, Y., *Biosci. Biotech. Biochem.* 1994, 58 (7), 1347-1348.
15. Spies, H. S. C.; Steenkamp, D. J., *Eur. J. Biochem.* 1994, 224, 203-213.
16. Newton, G. L.; Bewley, C. A.; Dwyer, T. J.; Horn, R.; Aharonowitz, Y.; Cohen, G.; Davies, J.; Faulkner, D. J.; Fahey, R. C., *Eur. J. Biochem.* 1995, 230, 821-825.
17. Newton, G. L.; Arnold, K.; Price, M. S.; Sherrill, C.; delCardayre, S. B.; Aharonowitz, Y.; Cohen, G.; Davies, J.; Fahey, R. C.; Davis, C., *J. Bact.* 1996, 178, 1990-1995.
18. Newton, G. L.; Buchmeier, N.; Fahey, R. C., *Microbiol. Mol. Biol. Rev.* 2008, 72, 471-494.
19. Knapp, S.; Gonzalez, S.; Myers, D. S.; Eckman, L. L.; Bewley, C. A., *Org. Lett.* 2002, 4 (24), 4337-4339.
20. Bornemann, C.; Jardine, M. A.; Spies, H. S. C.; Steenkamp, D. J., *Biochem. J.* 1997, 325, 623-629.
21. (a) Majumder, A. L.; Johnson, M. D.; Henry, S. A., *Biochimica et Biophysica Acta* 1997, 1348, 245-256; (b) Majumder, A. L.; Biswas, B. B., *Biology of Inositols and Phosphoinositides.* Springer: 2006.
22. Pollack, S. J.; Atack, J. R.; Knowles, M. R.; McAllister, G.; Ragan, C. I.; Baker, R.; Fletcher, S. R.; Iversen, L. I.; Broughton, H. B., *PNAS USA* 1994, 91, 5766-5770.
23. Sureshan, K. M.; Shashidhar, M. S.; Praveen, T.; Das, T., *Chem. Rev.* 2003, 103, 4477-4503.
24. (a) Haines, A. H., *Adv. Carbohydr. Chem. Biochem.* 1976, 33, 11-109; (b) Knapp, S.; Kukkola, P. J.; Sharma, S.; Dhar, T. G. M.; Naughton, A. B. J., *J. Org. Chem.* 1990, 55, 5700-5710.
25. Desai, T.; Gigg, J.; Gigg, R.; Payne, S.; Penades, S.; Rogers, H., *J. Carbohydr. Res.* 1992, 216, 197-209.
26. Shvets, V. I., *Russ. Chem. Rev.* 1974, 43, 488-502.

The invention claimed is:

1. A method of preparing pure or substantially pure D-myo-inositol-3-phosphate or derivative forms thereof, for use in further chemical reactions, comprising:
   a) contacting the enzyme D-myo-inositol-3-phosphate synthase (INO1) with glucose-6-phosphate and/or fructose-6-phosphate in order to generate D-myo-inositol-3-phosphate, wherein the INO1 is immobilized on a solid support through an N-terminal affinity tag; and
   b) optionally further reacting D-myo-inositol-3-phosphate with another enzyme or chemical to generate a further molecule; and
   c) purifying said D-myo-inositol-3-phosphate or said further molecule,
   wherein the INO1 is immobilized on the solid support prior to step a), and wherein the immobilized INO1 is separated from the solution comprising D-myo-inositol-3-phosphate or said further molecule, and any further reagents, by filtration.

2. A method of preparing pure or substantially pure D-myo-inositol-3-phosphate or derivative forms thereof, for use in further chemical reactions, comprising:
   a) contacting the enzyme D-myo-inositol-3-phosphate synthase (INO1) with glucose-6-phosphate and/or fructose-6-phosphate in order to generate D-myo-inositol- 3-phosphate, wherein the INO1 is immobilized on a solid support through an N-terminal affinity tag; and b) optionally further reacting D-myo-inositol-3-phosphate with another enzyme or chemical to generate a further molecule; and c) purifying said D-myo-inositol-3-phosphate or said further molecule, wherein the INO1 is immobilized on the solid support prior to step a), wherein the immobilized INO1 is retained within a column and the method further comprises:

flowing reagents into and through the column, so as to contact the INO1 with glucose-6-phosphate and/or fructose-6-phosphate; and flowing a solution comprising D-myo-inositol-3-phosphate product(s) out of the column, to thereby separate the INO1 enzyme therefrom.

3. The method according to claim 1 or 2, comprising converting D-myo-inositol-3-phosphate to myo-inositol, using myo-inositol-monophosphate phosphatase (IMPase).

4. The method according to claim 3, comprising protecting one or more hydroxy functional groups on D-myo-inositol-3-phosphate, so as to provide a protected compound suitable for use in further chemical synthesis.

5. The method according to claim 4, comprising protecting one or more hydroxy functional groups on D-myo-inositol-3-phosphate or myo-inositol, before or after generation of the myo-inositol, so as to provide a protected compound suitable for use in further chemical synthesis.

6. The method according to claim 1 or 2, wherein the INO1 enzyme is from *Trypanosoma brucei*.

7. The method according to claim 1 or 2, wherein the INO1 enzyme is physisorbed to the solid support.

8. The method according to claim 7, wherein the solid support comprises nickel or cobalt agarose beads, comprising a surface-immobilized nickel or cobalt chelate.

9. The method of claim 1 or 2, wherein the conversion of glucose-6-phosphate or fructose-6-phosphate by the INO1 enzyme is carried out in a buffered solution, buffered at between pH 7.5-8.5 and wherein optionally also present are $NAD^+$ and/or a reducing agent selected from DTT and ammonium acetate.

10. The method according to claim 9, wherein the buffer is ammonium bicarbonate; said buffer is removed through sublimation during the freeze-drying of the preparation comprising said D-myo-inositol-3-phosphate.

11. The method according to claim 1 or 2, wherein the glucose-6-phosphate and/or fructose-6-phosphate is labelled such that the generated D-myo-inositol-3-phosphate or said further molecule is labelled.

12. The method according to claim 1 or 2, wherein the glucose-6-phosphate and/or fructose-6-phosphate is protected such that the generated D-myo-inositol-3-phosphate or said further molecule is protected.

13. The method according to claim 2, wherein the product is purified by chromatographic means selected from High pressure liquid chromatography (HPLC) and ion-exchange chromatography.

14. The method according to claim 2, comprising flowing said solution through the column more than once.

15. The method according to claim 14, wherein the solution is collected from the column and all or a portion of the solution is re-introduced into the column.

16. The method according to claim 2, wherein the product(s) are purified using a continuous flow chromatographic method.

17. The method according to claim 2, comprising immobilizing a further enzyme or chemical and causing the solution to flow into, through and out of a column comprising said immobilized INO1 and subsequently into, through and out of a further column comprising said immobilized further enzyme or other chemical.

\* \* \* \* \*